United States Patent
Igarashi et al.

(10) Patent No.: US 10,481,122 B2
(45) Date of Patent: Nov. 19, 2019

(54) GAS SENSOR ELEMENT AND GAS SENSOR

(71) Applicant: NGK Spark Plug Co., LTD., Nagoya (JP)

(72) Inventors: Ai Igarashi, Konan (JP); Kouji Toida, Kani (JP); Shun Sakuma, Kakamigahara (JP)

(73) Assignee: NGK Spark Plug Co., LTD., Nagoya (JP)

( * ) Notice: Subject to any disclaimer, the term of this patent is extended or adjusted under 35 U.S.C. 154(b) by 275 days.

(21) Appl. No.: 15/498,074

(22) Filed: Apr. 26, 2017

(65) Prior Publication Data

US 2017/0315081 A1    Nov. 2, 2017

(30) Foreign Application Priority Data

Apr. 27, 2016  (JP) .................................. 2016-088752
Apr. 19, 2017  (JP) .................................. 2017-082720

(51) Int. Cl.
  *G01N 27/407*   (2006.01)
  *G01N 27/406*   (2006.01)

(52) U.S. Cl.
  CPC ..... *G01N 27/4077* (2013.01); *G01N 27/4067* (2013.01); *G01N 27/4071* (2013.01); *G01N 27/4073* (2013.01); *G01N 27/4076* (2013.01)

(58) Field of Classification Search
  None
  See application file for complete search history.

(56) References Cited

U.S. PATENT DOCUMENTS

| | | | |
|---|---|---|---|
| 6,068,747 A * | 5/2000 | Tojo | G01N 27/417 |
| | | | 204/425 |
| 2003/0089603 A1 | 5/2003 | Scheer et al. | |
| 2007/0144904 A1 | 6/2007 | Strohmaier et al. | |
| 2015/0276658 A1* | 10/2015 | Okazaki | G01N 27/4071 |
| | | | 204/431 |

FOREIGN PATENT DOCUMENTS

| | | | | |
|---|---|---|---|---|
| JP | H02298859 | * | 12/1990 | ........... G01N 27/409 |
| JP | 2007-512511 A | | 5/2007 | |
| JP | 4813729 B | | 11/2011 | |
| JP | 2015-194474 A | | 11/2015 | |

* cited by examiner

*Primary Examiner* — Gurpreet Kaur
*Assistant Examiner* — Steven E Rosenwald
(74) *Attorney, Agent, or Firm* — Leason Ellis LLP

(57) ABSTRACT

A gas sensor element comprises a solid electrolyte layer; a detection electrode provided on one surface of the solid electrolyte layer; a reference electrode provided on another surface of the solid electrolyte layer; a first layer provided on a side where the other surface of the solid electrolyte layer is present, and having a reference gas flow path; and a heater layer provided on a side opposite to a side where the solid electrolyte layer is provided. In the gas sensor element, an introduction flow path is formed as a flow path for guiding the reference gas from outer surfaces of the gas sensor element to the reference gas flow path. The introduction flow path has an opening provided at an outer surface that is perpendicular to a stacking direction of the gas sensor element and is provided on a side opposite to the heater layer.

7 Claims, 8 Drawing Sheets

GAS SENSOR ELEMENT AND GAS SENSOR

This application claims the benefit of Japanese Patent Applications No. 2016-088752, filed Apr. 27, 2016 and No. 2017-082720, filed Apr. 19, 2017, all of which are incorporated herein in their entireties by reference.

FIELD OF THE INVENTION

The present invention relates to a gas sensor element and a gas sensor.

BACKGROUND OF THE INVENTION

Conventionally, there is known a gas sensor for detecting the concentration of a specific gas component in an exhaust gas emitted from an internal combustion engine of an automobile or the like. A gas sensor element used in the gas sensor generally includes a solid electrolyte layer, and a reference electrode and a detection electrode that are provided on the surfaces of the solid electrolyte layer. A reference gas (e.g., air) is supplied to the reference electrode, and a gas to be measured is supplied to the detection electrode. As the gas sensor element, for example, there is known a stacked type gas sensor element that includes a stacked body in which, together with the above-described solid electrolyte layer including the pair of electrodes, an insulating layer, a heater, and the like are stacked, and that has a plate-like outer shape as a whole. As a structure in which a reference gas is supplied to the reference electrode in the stacked type gas sensor element, there is proposed a structure in which, in a layer adjacent to the reference electrode, a through-hole is provided so as to form a reference gas chamber that supplies a reference gas to the reference electrode and a through-hole is provided so as to form a communication path for guiding the reference gas from a side surface of the stacked type gas sensor element to the reference gas chamber (e.g., see Patent Document 1).

PRIOR ART DOCUMENT

Patent Document

[Patent Document 1] Japanese Patent No. 4813729
[Patent Document 2] Japanese Patent Application Laid-Open (kokai) No. 2015-194474
[Patent Document 3] Japanese Patent Application Laid-Open No. 2007-512511

Problems to be Solved by the Invention

In the above-described gas sensor, it is desirable that a sufficient amount of the reference gas is flowed to the reference electrode without delay. As a measure to secure a smooth flow of the reference gas to the reference electrode as described above, for example, a measure to further shorten the length of the path from a reference gas intake port at the outer surface of the gas sensor element to the reference gas chamber (to further shorten the total length of the communication path), and a measure to further enlarge a flow path sectional area of the communication path, are considered. However, in the gas sensor element in which the reference gas chamber and the communication path are provided in the same surface of the layer adjacent to the reference electrode as described above, even when the length of the communication path is attempted to be shortened, the communication path usually needs to be bent due to a restriction caused by the entire structure of the gas sensor element (e.g., a restriction that a through-hole provided in the gas sensor element should be bypassed), which makes it difficult to secure a large flow path sectional area thereof. In the gas sensor, the gas sensor element may receive pressing forces from various directions, and, especially, is greatly affected by a force directed to a stacked surface having a large area, that is, a pressing force in a stacking direction. In the gas sensor element, when the pressing force is applied in the stacking direction of the gas sensor element, there arises a problem that the communication path is likely to be deformed in a position in which the flow path cross section of the communication path is large. When the communication path is deformed, stable introduction of the reference gas into the reference gas chamber is hampered.

SUMMARY OF THE INVENTION

Means for Solving the Problems

The present invention has been made to solve the above problem and can be embodied in the following modes.

(1) According to an aspect of the present invention, a gas sensor element comprises: a solid electrolyte layer; a detection electrode provided on one surface of the solid electrolyte layer and exposed to a gas to be measured; a reference electrode provided on another surface of the solid electrolyte layer and exposed to a reference gas; a first layer provided on a side where the other surface of the solid electrolyte layer is present, and having a reference gas flow path that introduces the reference gas into the reference electrode; and a heater layer provided on a side opposite to a side where the solid electrolyte layer is provided with respect to the first layer, the heater layer including a heating portion for heating the solid electrolyte layer. In the gas sensor element, the solid electrolyte layer, the first layer and the heater layer are stacked, an introduction flow path is formed as a flow path for guiding the reference gas from multiple outer surfaces of the gas sensor element to the reference gas flow path, the introduction flow path has an opening provided at one of the multiple outer surfaces that is perpendicular to a stacking direction of the gas sensor element and is provided on a side opposite to the side where the heater layer is provided with respect to the first layer, and the introduction flow path extends in the stacking direction from the opening to the reference gas flow path.

According to the gas sensor element of this aspect, inside the gas sensor element, it is possible to suppress bending of an introduction flow path for introducing the reference gas from the outer surface of the gas sensor element into the reference electrode. Therefore, it is easy to secure a flow path sectional area of the introduction flow path and to shorten the flow path length of the introduction flow path. Further, even when a pressing force is applied in the stacking direction of the gas sensor element, it is possible to suppress deformation of the introduction flow path. Therefore, it is possible to reliably introduce the reference gas into the reference electrode.

(2) In the gas sensor element according to the above aspect, a plurality of the openings may be provided, and the introduction flow path may be composed of a plurality of divided flow paths extending in the stacking direction from the respective openings to the reference gas flow path. According to the gas sensor element of this aspect, since a plurality of introduction flow paths extending in the stacking direction are provided, when the amount of the reference gas to be supplied to the reference electrode is secured, it is possible to decrease the size of the flow path cross section of each introduction flow path, and to increase the degree of freedom of arrangement of the introduction flow paths. Therefore, in the gas sensor element, it is easy to secure strength against the pressing force in the stacking direction.

(3) In the gas sensor element according to the above aspect, the plurality of openings may be provided at different positions with respect to a longitudinal direction of the gas sensor element. According to the gas sensor element of this aspect, it is possible to secure a longer distance between the individual openings in the layer provided at the end portion in the stacking direction, and to secure a longer distance between the individual introduction flow paths. Therefore, it is possible to suppress a reduction in strength of the gas sensor element, which is caused by providing the introduction flow paths.

(4) In the gas sensor element according to the above aspect, $D_A<D_B$ may be satisfied, where $D_A$ is a distance from the one of the multiple outer surfaces, in which the opening is provided, to the reference gas flow path, and $D_B$ is a distance from another of the multiple outer surfaces to the reference gas flow path. According to the gas sensor element of this aspect, since it is possible to shorten the distance from the outer surface of the gas sensor element to the reference gas flow path, it is easy to reliably supply the reference gas to the reference electrode. As a result, it is possible to improve gas detection accuracy.

(5) In the gas sensor element according to the above aspect, $D_A<D_C$ may be satisfied, where $D_A$ is a distance from the one of the multiple outer surfaces, in which the opening is provided, to the reference gas flow path, and $D_C$ is a distance from an end portion on a side closer to the introduction flow path to the reference gas flow path. According to the gas sensor element of this aspect, since it is possible to shorten the distance from the outer surface of the gas sensor element to the reference gas flow path, a stable supply of the reference gas to the reference electrode is facilitated. As a result, it is possible to improve gas detection accuracy.

(6) In the gas sensor element according to the above aspect, the solid electrolyte layer may include: an insulating substrate formed from an insulating ceramic; and a solid electrolyte portion formed from a solid electrolyte, and the solid electrolyte layer is provided to penetrate through the insulating substrate in a region that overlaps with the detection electrode and the reference electrode in the stacking direction. According to the gas sensor element of this aspect, it is possible to increase the strength of the entire sensor element, and as a result, to increase the strength of the entire gas sensor. In addition, when the gas sensor is used, it is possible to more quickly increase the temperature of the solid electrolyte portion to a predetermined active temperature.

The present invention can be embodied in various forms other than the above. For example, it is possible to embody the present invention in forms such as a gas sensor including a gas sensor element, a method of manufacturing the gas sensor element, a method of manufacturing the gas sensor, a method of supplying a reference gas to a reference electrode, etc.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

A. First Embodiment

Figure 1:
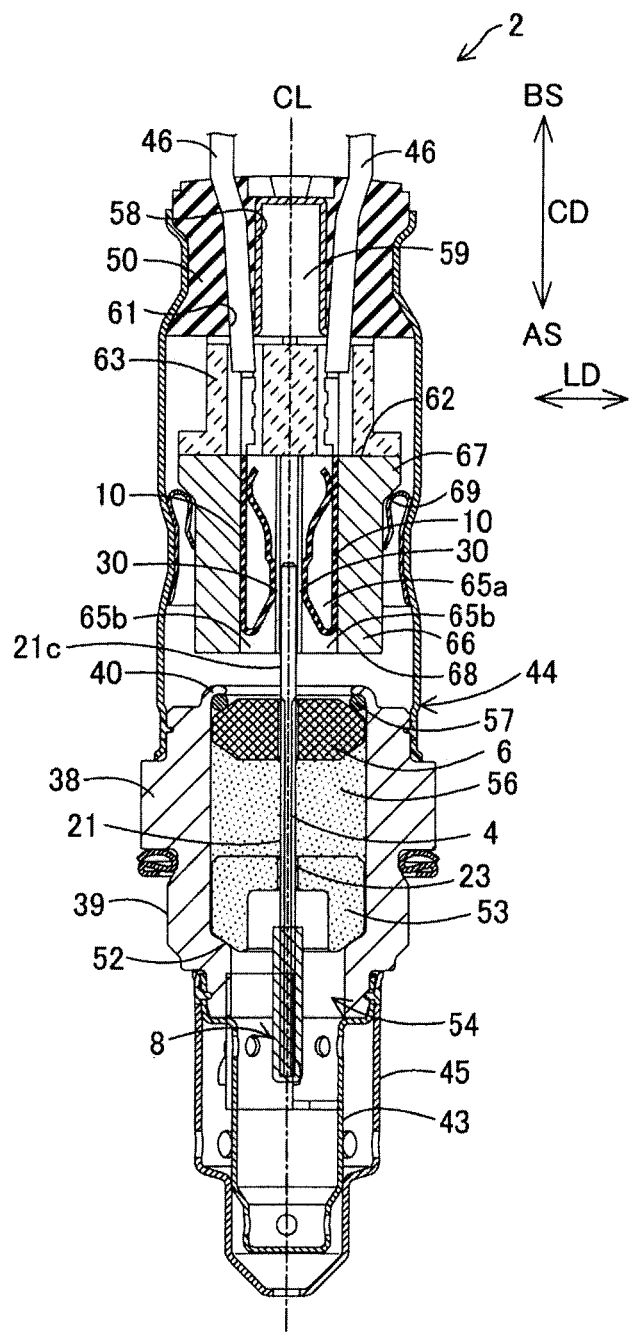
FIG. 1 is a sectional view of the entire structure of a gas sensor.

A-1. Structure of Gas Sensor:

FIG. 1 is a sectional view showing the entire structure of a gas sensor 2 as a first embodiment of the present invention. The gas sensor 2 is fixed to an exhaust pipe of an unillustrated internal combustion engine (engine) and measures the concentration of a specific gas contained in an exhaust gas that is a gas to be measured. The gas sensor 2 of the present embodiment is a sensor that measures an oxygen gas concentration. FIG. 1 shows a cross section that includes an axial line CL of the gas sensor 2 and that is in parallel with an axial direction CD that is a direction in parallel with the axial line CL. The axial line CL extends, at a center of the gas sensor 2, in the longitudinal direction of the gas sensor 2. In the following description, the lower side with respect to the sheet of FIG. 1 is referred to as a "front side AS", the upper side thereof is referred to as a "rear side BS", and a direction passing through the axial line CL and perpendicular to the axial line CL is referred to as a "radial direction".

The gas sensor 2 includes a plate-shaped sensor element 4 extending in the axial direction CD, a front side separator 66 in which the rear side BS of the sensor element 4 is inserted, a rear side separator 63 provided on the rear side BS of the front side separator 66, a metal terminal member 10 contacting with an electrode terminal portion 30 formed at the rear side BS of the sensor element 4, and a metal shell 38 surrounding the periphery of the sensor element 4 at a position on the front side AS relative to the front side separator 66. Four electrode terminal portions 30 and four metal terminal members 10 are provided. In FIG. 1, only two electrode terminal portions 30 and two metal terminal members 10 are illustrated.

The sensor element 4 outputs a signal for detecting the oxygen concentration in an exhaust gas which is the gas to be measured. In the plate-shaped sensor element 4, a first plate surface 21 and a second plate surface 23 that is an opposite surface from the first plate surface 21 constitute a main surface that is the largest surface. As described below, the sensor element 4 is formed by stacking a plurality of sheet-like members. In FIG. 1, a direction which is perpendicular to the axial direction CD and in which the above-described sheet-like members are stacked is represented as a stacking direction LD. The first plate surface 21 and the second plate surface 23 are the outer surfaces perpendicular to the stacking direction LD, of the outer surfaces of the sensor element 4.

The sensor element 4 includes a detection portion 8 located at the front side AS and exposed to the gas to be measured, four electrode terminal portions 30 located at the rear side BS and contacting with the corresponding metal terminal members 10. Two of the four electrode terminal portions 30 are formed on the first plate surface 21, and the remaining two are formed on the second plate surface 23. The sensor element 4 is fixed inside the metal shell 38 such that the detection portion 8 projects from the front end of the metal shell 38, and the electrode terminal portions 30 project from the rear end of the metal shell 38. Details of the sensor element 4 will be described below. In the present embodiment, the detection portion 8 of the sensor element 4 at the front side AS is covered with a protection layer formed from a porous material, thus suppressing accumulation of an impurity (e.g., water) contained in the gas to be measured to the detection portion 8. In the present embodiment, the "sensor element 4" serves as a "gas sensor element".

The front side separator 66 and the rear side separator 63 are formed from an insulating material such as alumina. The front side separator 66 is substantially tubular. The front side separator 66 is provided so as to surround the periphery of a rear side portion of the sensor element 4 where the electrode terminal portion 30 is located. The front side separator 66 includes an insertion portion 65a for inserting the rear side portion of the sensor element 4 therethrough, and four groove portions 65b (only two are illustrated in FIG. 1) formed on an inner wall surface of the insertion portion 65a. The four groove portions 65b extend in the axial direction CD, and penetrate from a front side end surface 68 to the rear side end surface 62 of the front side separator 66. The corresponding metal terminal members 10 are inserted in the four groove portions 65b. The front side separator 66 includes a flange portion 67 projecting radially outward toward the rear side BS. The rear side separator 63 has through-holes penetrating inside thereof along the axial direction CD, and rear end portions of the above-described metal terminal members 10 are inserted in the through-holes.

Each metal terminal member 10, inserted in the corresponding groove portion 65b, is located between the sensor element 4 and the front side separator 66 in the stacking direction LD. The metal terminal member 10 is held by the sensor element 4 and the front side separator 66. The metal terminal member 10 forms a current path between the sensor element 4 and an external device for calculating the oxygen concentration. The rear end portion of the metal terminal member 10 is electrically connected to a lead wire 46 arranged from outside to inside of the gas sensor 2 in the rear side separator 63, and is electrically connected to the corresponding electrode terminal portion 30 of the sensor element 4 in the front side separator 66. Four lead wires 46 are provided corresponding to the number of the electrode terminal portions 30, and are electrically connected to the external device (only two are illustrated in FIG. 1).

The metal shell 38 is a substantially tubular metallic member. The metal shell 38 includes a through-hole 54 penetrating therethrough in the axial direction CD, and a shelf portion 52 projecting radially inward of the through-hole 54. The metal shell 38 holds the sensor element 4 in the through-hole 54 such that the detection portion 8 is located at the front side AS relative to the opening of the through-hole 54 at the front side AS and each electrode terminal portion 30 is located at the rear side BS relative to the opening of the through-hole 54 at the rear side BS. The shelf portion 52 is formed as an inwardly tapered surface having a tilt with respect to a plane perpendicular to the axial direction CD. The outer surface of the metal shell 38 has a screw portion 39 for fixing the gas sensor 2 to the exhaust pipe.

Inside the through-hole 54, an annular ceramic holder 53, a powder-charged layer (talc ring) 56, and a ceramic sleeve 6 are stacked in order from the front side AS to the rear side BS so as to surround a radial periphery of the sensor element 4. A crimping packing 57 is provided between the ceramic sleeve 6 and a rear end portion 40 of the metal shell 38. The rear end portion 40 of the metal shell 38 is crimped through the crimping packing 57 so as to press the ceramic sleeve 6 toward the front side.

The gas sensor 2 further includes a sheath 44 fixed to the outer periphery of the metal shell 38 at the rear side BS of the metal shell 38, a holding member 69 for holding the front side separator 66, a grommet 50 provided at the rear end portion of the sheath 44, and an external protector 45 and an internal protector 43 which are fixed to the outer periphery of the metal shell 38 at the front side AS.

The sheath 44 is a substantially tubular metallic member. The outer periphery of the sheath 44 at the front side AS is attached to the metal shell 38 by laser welding or the like. The sheath 44 has an outer diameter decreasing at the rear side BS, and the grommet 50 is fitted in the opening having a diameter which is decreased. The grommet 50 has four lead wire insertion holes 61 (only two are illustrated in FIG. 1) in which the lead wires 46 are inserted.

The grommet 50 further has a through-hole 58 penetrating through a center portion thereof along the axial line CL. The through-hole 58 is filled with a filter unit 59 composed of a filter and a cylindrical metallic member for fixing the filter. Through the filter unit 59, air is introduced into the sheath 44. As described above, a space within the sheath 44 is filled with air.

The holding member 69 is a cylindrical metallic member. The holding member 69 is fixed to the sheath 44 and is positioned in the sheath 44. The holding member 69 holds the front side separator 66 by contacting with the flange portion 67 of the front side separator 66 at the rear side BS.

The external protector 45 and the internal protector 43 each are a metallic member having a bottomed tubular shape and a plurality of holes. The external protector 45 and the internal protector 43 are attached to the outer periphery of the metal shell 38 at the front side AS by laser welding or the like. The external protector 45 and the internal protector 43 protect the sensor element 4 by covering the detection portion 8. The gas to be measured passes through the plurality of holes provided in the external protector 45 and the internal protector 43, to flow into the internal protector 43.

Figure 2:
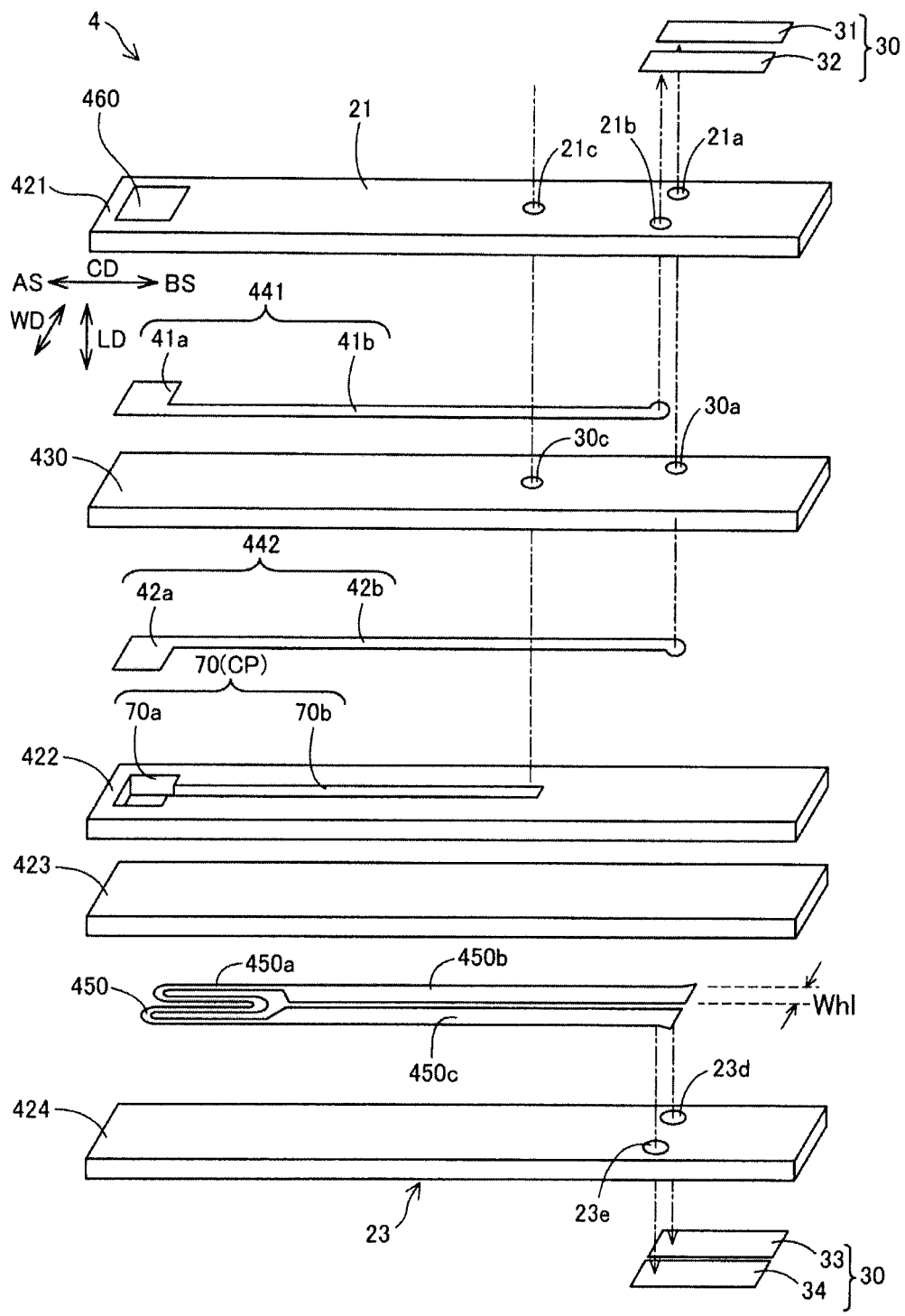
FIG. 2 is an exploded perspective view of a sensor element.

A-2. Structure of Sensor Element:

FIG. 2 is an exploded perspective view of the sensor element 4. The axial direction CD, the front side AS, the rear side BS, and the stacking direction LD shown in FIG. 2 correspond to the respective directions shown in FIG. 1. The sensor element 4 includes an insulating layer 421, a detection electrode 441, a solid electrolyte layer 430, a reference electrode 442, a gas flow path formation layer 422, an insulating layer 423, a heater 450, and an insulating layer 424. The components are stacked in order along the stacking direction LD. The insulating layer 421, the solid electrolyte layer 430, the gas flow path formation layer 422, and the insulating layers 423, 424 are each a rectangular sheet-like member, and have substantially the same outer shape.

In FIG. 2, the four electrode terminal portions 30 (specifically, electrode terminal portions 31 to 34) are also illustrated. Each of the electrode terminal portions 30 is used for electrical connection to the sensor element 4. Each electrode terminal portion 30 is formed by use of, for example, platinum, rhodium, or the like and has a substantially rectangular shape. Each electrode terminal portion 30 can be formed, for example, by performing screen printing of a paste including platinum or the like as a principal component on the insulating layer 421 or the insulating layer 424. At the rear side BS of the sensor element 4, the electrode terminal portions 31, 32 are formed to be arranged side by side in the direction perpendicular to the axial direction CD on the first plate surface 21 of the insulating layer 421. At the rear side BS of the sensor element 4, the electrode terminal portions 33, 34 are formed to be arranged side by side in the direction perpendicular to the axial direction CD on the second plate surface 23 of the insulating layer 424. In FIG. 2, a direction in parallel with the first plate surface 21 and the second plate surface 23 and perpendicular to the axial direction CD is represented as a width direction WD.

The solid electrolyte layer 430 serves as an oxygen concentration cell that detects the oxygen concentration in the exhaust gas, in cooperation with the detection electrode 441 and the reference electrode 442. The solid electrolyte layer 430 is formed from a solid electrolyte having oxide ion conductivity (oxygen ion conductivity). In the present embodiment, the solid electrolyte layer 430 is formed from zirconium oxide ($ZrO_2$) to which yttrium oxide ($Y_2O_3$) is added as a stabilizer, that is, yttria-stabilized zirconia (YSZ). Alternatively, the solid electrolyte layer 430 may be formed from another type of solid electrolyte. Specifically, the solid electrolyte layer 430 may be formed from another zirconia-based solid electrolyte such as stabilized zirconia to which an oxide selected from among calcium oxide (CaO), magnesium oxide (MgO), cerium oxide ($CeO_2$), scandium oxide ($Sc_2O_3$), and the like is added. The solid electrolyte layer 430 has through-holes 30a, 30c penetrating through the solid electrolyte layer 430 in the thickness direction (the stacking direction LD) thereof. The through-hole 30a is provided at an end portion of the solid electrolyte layer 430 on the rear side BS, and a through-hole 30c is provided at the front side AS relative to the through-hole 30a.

The insulating layers 421, 423, 424 each are a dense layer that electrically insulates between the adjacent layers. The insulating layers 421, 423, 424 are formed from an insulating ceramic, for example, an insulating ceramic including alumina as a principal component. At the front side AS of the insulating layer 421, a rectangular hole penetrating through the insulating layer 421 in the thickness direction (the stacking direction LD) thereof is provided, and a porous protection layer 460 is formed in the hole. The porous protection layer 460 is a porous layer formed from alumina or the like, and is provided to diffuse the gas to be measured that flows to the detection electrode 441. It is noted that in the sensor element 4, a portion including the porous protection layer 460 at the front side AS is included in the detection portion 8 described above. In addition, the rear side BS of the insulating layer 421 has three through-holes 21a, 21b, 21c penetrating through the insulating layer 421 in the stacking direction LD. Similarly, the rear side BS of the insulating layer 424 has two through-holes 23d, 23e penetrating through the insulating layer 424 in the thickness direction (the stacking direction LD) thereof.

The detection electrode 441 is formed, for example, by use of platinum, rhodium, or the like. The detection electrode 441 is provided on one surface (a surface on a side where the insulating layer 421 is provided), in the stacking direction LD, of the solid electrolyte layer 430. The detection electrode 441 includes a first electrode portion 41a provided at an end portion thereof on the front side AS, and a first lead portion 41b extending from the first electrode portion 41a toward the rear side BS. The detection electrode 441 is electrically connected to the electrode terminal portion 32 from the end portion of the first lead portion 41b on the rear side BS through a through-hole 21b of the insulating layer 421.

The reference electrode 442 is formed, for example, by use of platinum, rhodium, or the like. The reference electrode 442 is provided on the other side (a surface on a side where the gas flow path formation layer 422 is provided), in the stacking direction LD, of the solid electrolyte layer 430. The reference electrode 442 includes a second electrode portion 42a provided at an end portion thereof on the front side AS, and a second lead portion 42b extending from the second electrode portion 42a toward the rear side BS. The reference electrode 442 is electrically connected to the electrode terminal portion 31 from the second lead portion 42b through the through-hole 30a of the solid electrolyte layer 430 and the through-hole 21a of the insulating layer 421.

The gas flow path formation layer 422 is formed from a dense ceramic. The gas flow path formation layer 422 has an introduction hole 70 that is a through-hole penetrating through the gas flow path formation layer 422 in the thickness direction (the stacking direction LD) thereof and that is for forming a reference gas flow path CP for introducing a reference gas to the reference electrode 442. In the present embodiment, air is used as the reference gas. The introduction hole 70 includes a reference chamber hole 70a formed in a rectangular shape in a plan view at the end portion on the front side AS, and a ventilation hole 70b that is smaller in width than the reference chamber hole 70a and that extends from the reference chamber hole 70a toward the rear side BS. In addition, the introduction hole 70 is enclosed by the gas flow path formation layer 422, the solid electrolyte layer 430 having a surface in which the reference electrode 442 is formed, and the insulating layer 423, thereby forming the reference gas flow path CP that introduces the reference gas into the reference electrode 442. That is, the gas flow path formation layer 422 serves as the "first layer" having the reference gas flow path for introducing the reference gas into the reference electrode 442. Details of the reference gas flow path CP will be described below.

Between the insulating layer 423 and the insulating layer 424, a heater 450 extending along the axial direction CD is embedded. The heater 450 is used to increase the temperature of the sensor element 4 to a predetermined active temperature, so that oxygen ion conductivity in the solid electrolyte layer 430 is increased and the operation of the gas sensor 2 is stabilized. The heater 450 is a resistive heating element formed from a conductor such as platinum, and generates heat by use of supplied power.

The heater 450 includes a heating portion 450a formed in a meandering manner at the front side AS, and heater lead portions 450b, 450c connected to the opposed ends of the heating portion 450a and linearly extending toward the rear side BS. The end portions of the heater lead portions 450b, 450c on the rear side BS are electrically connected to the electrode terminal portions 33, 34 through the through-holes 23d, 23e formed in the insulating layer 424, respectively. In the present embodiment, the heater 450 serves as a "heater layer" including the heating portion 450a for heating the solid electrolyte layer 430.

Figure 3:
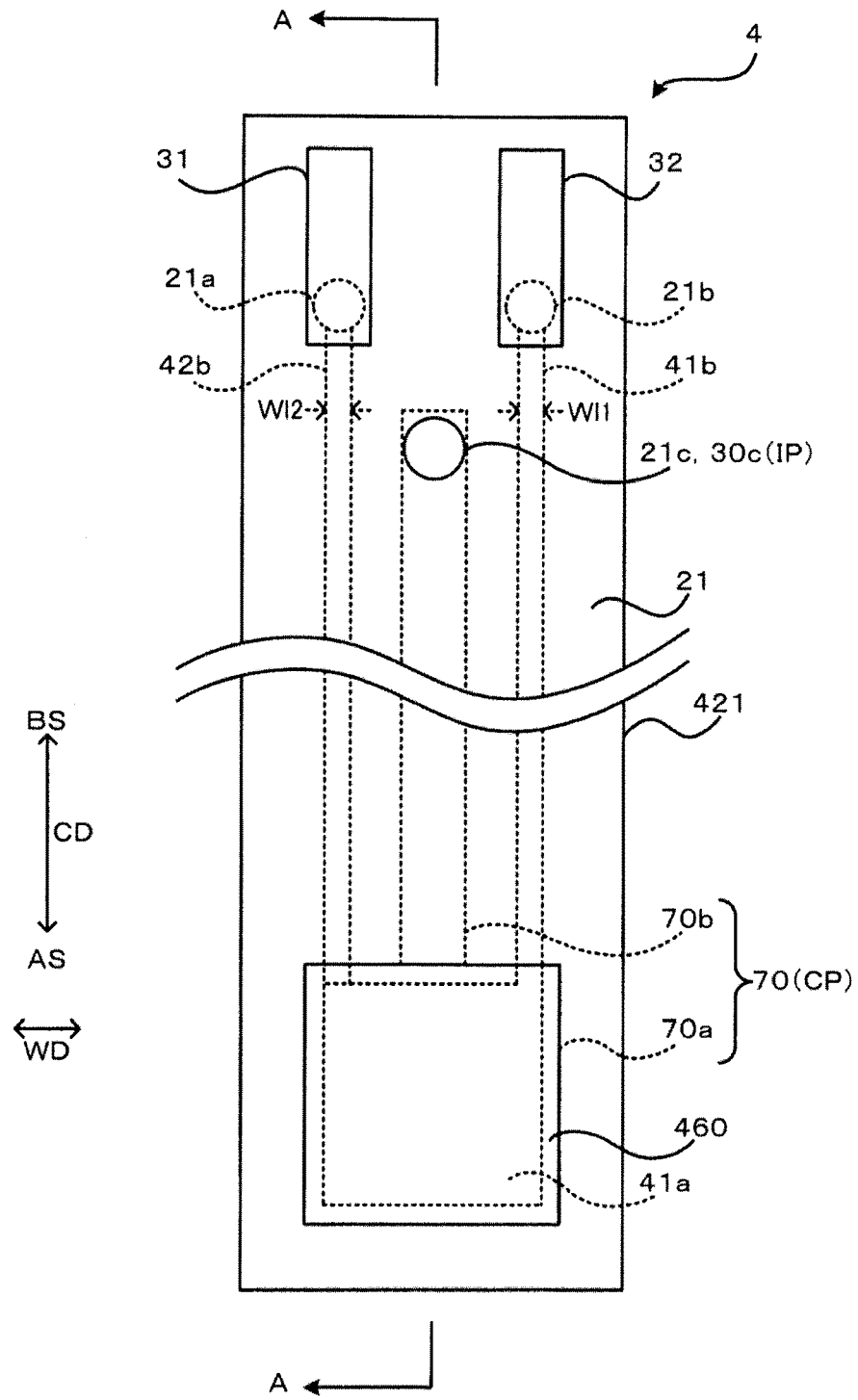
FIG. 3 is a plan view of the sensor element.
Figure 4:
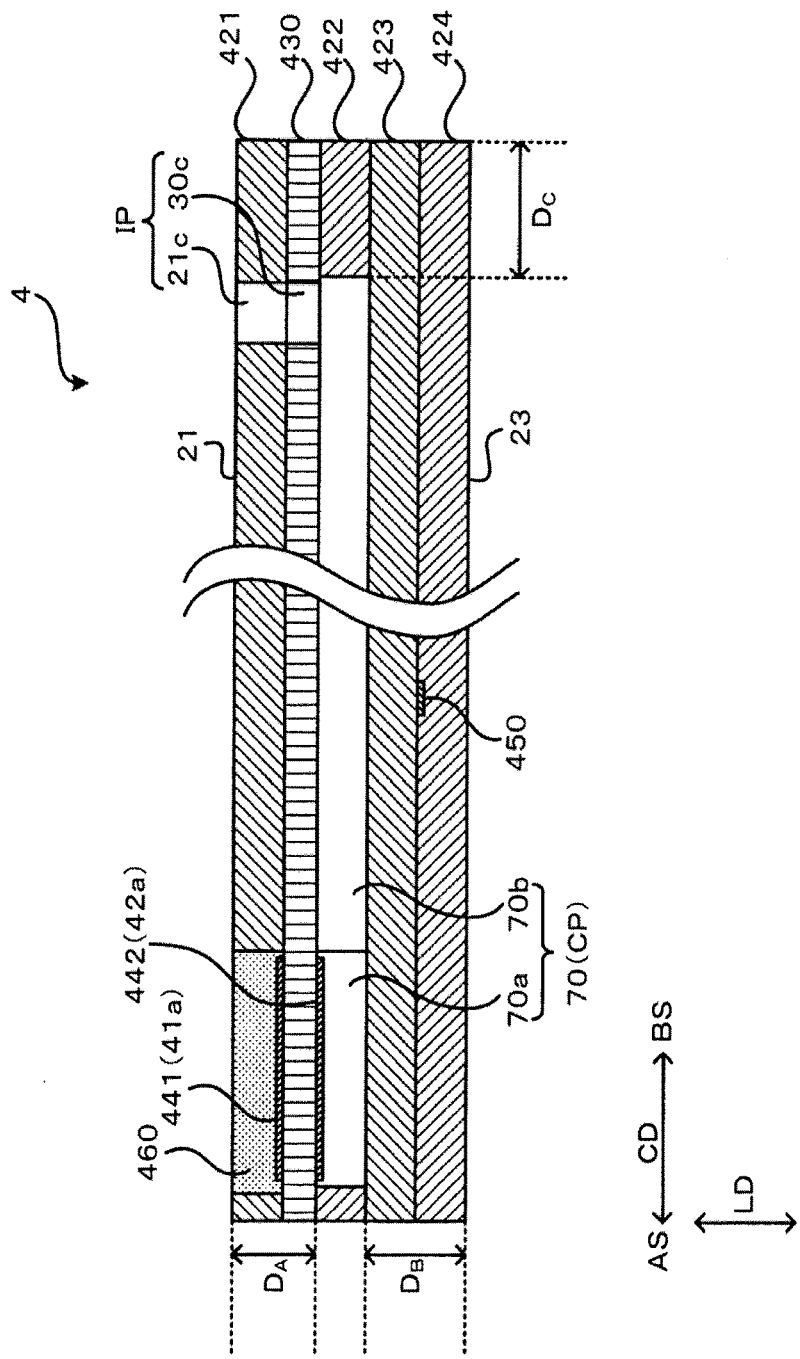
FIG. 4 is a sectional view of the sensor element in an A-A cross section in FIG. 3.

A-3. Structure of Reference Gas Flow Path:

FIG. 3 is a plan view of the sensor element 4 as seen from the first plate surface 21 side. In addition, FIG. 4 is a sectional view of the sensor element 4 in an A-A cross section shown in FIG. 3. In FIG. 3, a structure appearing on the first plate surface 21 of the insulating layer 421 is represented by a solid line, and an internal structure of the sensor element 4 is represented by a broken line. It is noted that although the stacking direction LD is not illustrated in FIG. 3, the stacking direction LD in FIG. 3 is a direction perpendicular to the sheet. In addition, although the width direction WD is not illustrated in FIG. 4, the width direction WD in FIG. 4 is the direction perpendicular to the sheet.

As described above, the introduction hole 70 formed in the gas flow path formation layer 422 and forming the reference gas flow path CP includes the reference chamber hole 70a and the ventilation hole 70b. As shown in FIG. 3, the reference chamber hole 70a, when being projected in the stacking direction LD, is provided at a position that overlaps with the entirety of the first electrode portion 41a in the detection electrode 441 and the entirety of the second electrode portion 42a in the reference electrode 442. That is, the second electrode portion 42a of the reference electrode 442 is exposed in a space that is a part of the reference gas flow path CP and that is formed by the reference chamber hole 70a.

As shown in FIG. 3, the end portion of the ventilation hole 70b on the rear side BS, when being projected in the stacking direction LD, overlaps with the entirety of the through-hole 21c provided in the insulating layer 421 and the entirety of the through-hole 30c provided in the solid electrolyte layer 430. As shown in FIG. 4, the through-hole 21c in the insulating layer 421 and the through-hole 30c in the solid electrolyte layer 430 form an introduction flow path IP that is a flow path extending in the stacking direction LD from the outer surface (the first plate surface 21) of the sensor element 4 to the reference gas flow path CP, and guiding the reference gas. Therefore, in the sensor element 4, the reference gas is taken in the reference gas flow path CP through the introduction flow path IP having an opening in the first plate surface 21 of the insulating layer 421, and the second electrode portion 42a of the reference electrode 442 is exposed to the reference gas (see FIG. 2). As shown in FIG. 1, the opening of the introduction flow path IP in the first plate surface 21 (the opening of the through-hole 21c in the insulating layer 421) is provided, inside the gas sensor 2, between a region in which the sensor element 4 is enclosed by the metal shell 38 and a region in which the sensor element 4 is enclosed by the front side separator 66. Accordingly, the above-described opening is exposed to air, whereby air that is the reference gas can be introduced into the introduction flow path IP.

According to the gas sensor 2 of the present embodiment having the above-described structure, the introduction flow path IP for guiding the reference gas to the reference gas flow path CP extends in the stacking direction from the opening provided in the first plate surface 21 that is the surface of the sensor element 4 to the reference gas flow path CP. Therefore, the flow path for introducing the reference gas from the outer surface of the sensor element 4 into the reference electrode 442 is suppressed from being bent due to, for example, the necessity of bypassing the other components in the sensor element 4. Since bending of the flow path is thus suppressed by providing the flow path in parallel with the stacking direction, it is easy to secure a flow path sectional area of the flow path and to shorten the length of the flow path. Further, even when the sensor element 4 receives the pressing force in the stacking direction LD, the introduction flow path IP in parallel with the stacking direction LD is unlikely to cause a problem that gas flow is hampered due to deformation of the introduction flow path IP. As described above, the flow of the reference gas to the reference electrode 442 can be stabilized. In addition, the performance of the gas sensor 2 can be stabilized by stabilizing the flow of the reference gas to the reference electrode 442.

Further, in the sensor element 4 of the present embodiment, the heater 450 is provided on a side opposite to the side where the solid electrolyte layer 430 is provided with respect to the gas flow path formation layer 422. In addition, the introduction flow path IP for guiding the reference gas to the reference gas flow path CP has an opening in the first plate surface 21 (the outer surface on a side opposite to the side where the heater 450 is provided with respect to the solid electrolyte layer 430) of the outer surfaces of the sensor element 4, and extends in the stacking direction LD from the opening to the reference gas flow path CP. Since the introduction flow path IP does not pass through the layer in which the heater 450 is formed, arrangement of the introduction flow path IP and the corresponding opening is not restricted by the wiring state of the heater 450.

In the present embodiment, a width Wh1 of each of heater lead portions 450b, 450c of the heater 450 (in FIG. 2, the width Wh1 of the heater lead portion 450b is shown) is formed to be larger than a width Wl1 of the first lead portion 41b of the detection electrode 441 and a width Wl2 (see FIG. 3) of the second lead portion 42b of the reference electrode 442. That is, the introduction flow path IP may be provided so as to avoid the first lead portion 41b and the second lead portion 42b having the smaller widths, and is not affected by the positions of heater lead portions 450b, 450c having the larger widths. Therefore, by providing the introduction flow path IP on the side opposite to the side where the heater 450 is provided with respect to the solid electrolyte layer 430, the degree of freedom of design regarding arrangement of (the opening of) the introduction flow path IP can be increased. It is noted that the width Wh1 of each of the heater lead portions 450b, 450c, the width of the first lead portion 41b, and the width Wl2 of the second lead portion 42b correspond to the lengths, in the width direction WD, of the heater lead portions 450b, 450c, the first lead portion 41b, and the second lead portion 42b, respectively.

In the present embodiment, the introduction flow path IP is provided such that, when being projected in parallel with the stacking direction LD, the entirety of the introduction flow path IP overlaps with the ventilation hole 70b. Thus, in a connection portion of the introduction flow path IP and the reference gas flow path CP, it is possible to suppress the flow of the reference gas from being hampered. However, the introduction flow path IP can also be provided such that, when being projected in the stacking direction LD, a part of the introduction flow path IP protrudes from the ventilation hole 70b without overlapping with the ventilation hole 70b.

Further, in the present embodiment, the flow path sectional area of the introduction flow path IP is smaller than the flow path sectional area of the reference gas flow path CP formed by the ventilation hole 70b. As described above, when the flow of the reference gas is throttled by the introduction flow path IP at the upstream side of the reference gas flow path CP, it is possible to accurately adjust the introduction amount of the reference gas to the reference gas flow path CP by use of the cross-sectional area of the introduction flow path IP. Alternatively, the flow path sectional area of the introduction flow path IP can also be made larger than the flow path sectional area of the reference gas flow path CP in the ventilation hole 70b. With this structure, since the flow of the reference gas is not throttled at the upstream side of the reference gas flow path CP, it is easy to secure the introduction amount of the reference gas to the reference electrode 442.

B. Second Embodiment

Figure 5:
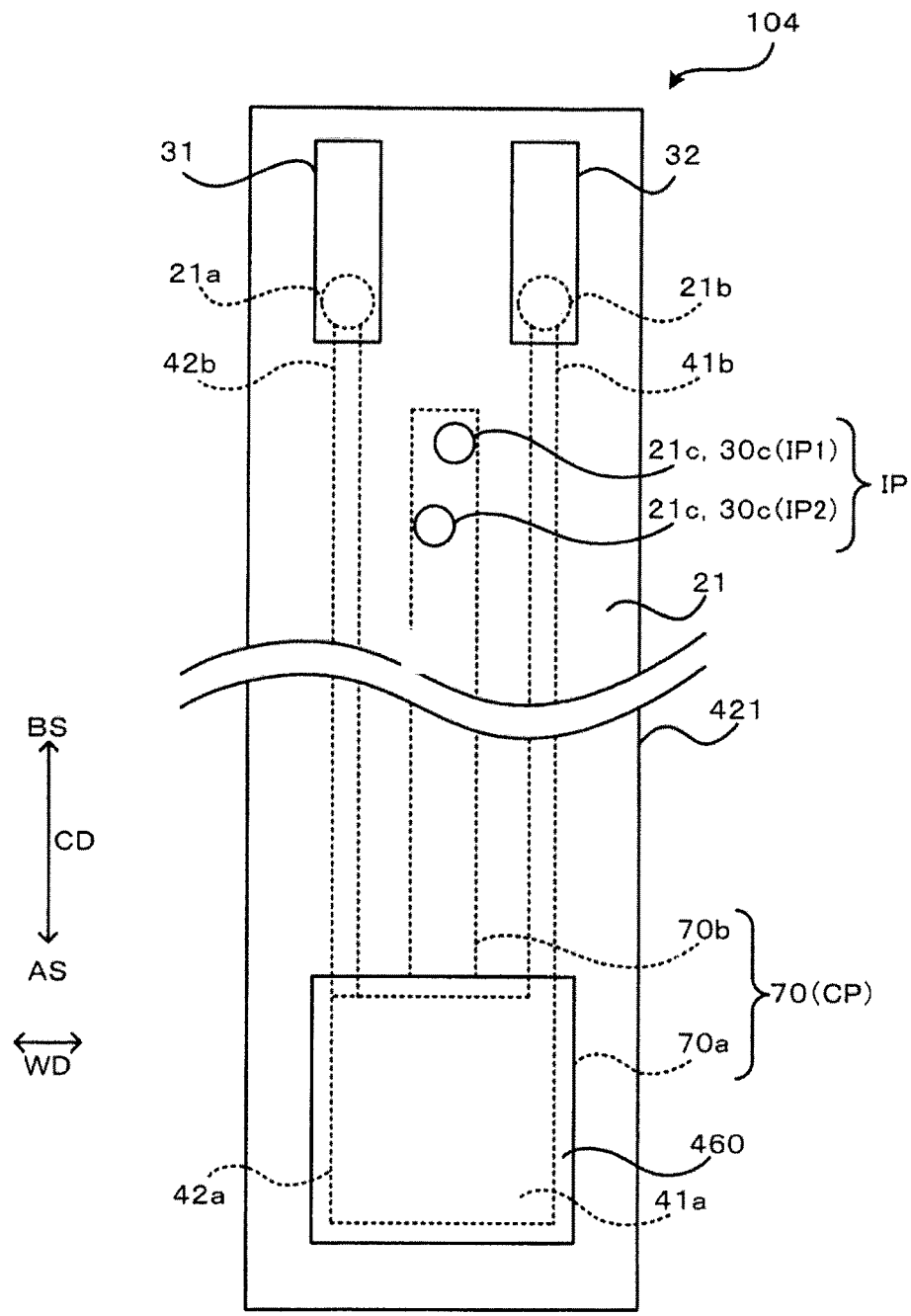
FIG. 5 is a plan view of the sensor element.

FIG. 5 is a plan view of a sensor element 104 of the second embodiment of the present invention, as seen from the first plate surface 21 side. In FIG. 5, as in FIG. 3, a structure appearing on the first plate surface 21 of the insulating layer 421 is represented by a solid line, and an internal structure of the sensor element 104 is represented by a broken line. It is noted that although FIG. 5 does not illustrate the stacking direction LD, the stacking direction LD is the direction perpendicular to the sheet of FIG. 5. The sensor element 104 of the second embodiment is used in the gas sensor 2, like the sensor element 4 of the first embodiment, and the structure of the sensor element 104 is similar to that of the sensor element 4 except the structure regarding the introduction flow path IP. Hereinafter, the same reference numbers are assigned to the same parts as those of sensor element 4, and a detailed description thereof is omitted.

In the sensor element 104, the introduction flow path IP extending in the stacking direction LD from the outer surface of the sensor element 104 to the reference gas flow path CP and introducing the reference gas is composed of two divided flow paths IP1, IP2. Each of the divided flow paths IP1, IP2 includes, as in the first embodiment, an opening in the first plate surface 21. In the second embodiment, since the introduction flow path IP extending in the stacking direction LD is composed of the two divided flow paths IP1, IP2, when the amount of the reference gas introduced into the reference gas flow path CP is secured, the cross-sectional area of the individual flow path can be made smaller as compared to the case where the introduction flow path IP is composed of a single flow path. Therefore, the strength against the pressing force in the stacking direction LD can be increased in the sensor element 104. Further, in the introduction flow path IP, since the cross-sectional area of the individual flow path can be made small, the degree of freedom in arranging the individual flow paths with respect to the stack surface (arrangement of the individual flow paths when being projected, in parallel with the stacking direction LD, on the first plate surface 21) can be increased.

In the second embodiment, the divided flow paths IP1, IP2 forming the introduction flow path IP are provided such that, when being projected in parallel with the stacking direction LD, the entireties of the respective flow paths, as in the first embodiment, overlap with the ventilation hole 70b. In this case, it is possible to adjust the introduction amount of the reference gas into the reference gas flow path CP by the total of the flow path sectional areas of the two divided flow paths IP1, IP2.

Further, in the second embodiment, the two divided flow paths IP1, IP2 extending in the stacking direction LD, as shown in FIG. 5, when being projected in the stacking direction LD, are provided at different positions with respect to the axial direction CD. That is, in the first plate surface 21, the openings of the two divided flow paths IP1, IP2 are provided at different positions with respect to a longitudinal direction of the sensor element 104 (shifted from each other in the axial direction CD). Although the two divided flow paths IP1, IP2 may be provided at the same position with respect to the axial direction CD, the structure as shown in FIG. 5 makes it easier to secure a distance between the two divided flow paths IP1, IP2. Therefore, it is possible to enhance the effect of suppressing a reduction in strength of the sensor element 104, which is caused by providing the introduction flow path IP. Further, when the two divided flow paths IP1, IP2 are provided, as shown in FIG. 5, the positions thereof when being projected in the stacking direction LD are desirably different positions with respect to the width direction WD (shifted from each other in the width direction WD). As described above, it is easier to secure a distance between the two divided flow paths IP1, IP2. It is noted that the positional shifting between the respective divided flow paths in the axial direction CD or the width direction WD means shifting, in the above-described direction, between the gravity center positions of the external shapes of the flow path cross sections of the respective divided flow paths when being projected in the stacking direction LD.

Although in the second embodiment, the number of the divided flow paths constituting the introduction flow path IP is two, the number may be more than two. Also in this case, by shifting the positions of the plurality of divided flow paths when being projected in the stacking direction LD, in the axial direction CD or the width direction WD, it is possible to suppress a reduction in strength of the sensor element caused by providing the introduction flow path IP.

C. Modified Embodiment

Modified Embodiment 1

Although in the above-described embodiments, the sensor element is composed of a plurality of sheet-like members shown in FIG. 2, the sensor element may have a different structure. For example, the sensor element may be a stacked body to which other sheet-like members are further added. Also in the case where the structure of the stacked body forming the sensor element is modified, it is desirable to make the length of the introduction flow path IP shorter. Specifically, in a case where a distance from one of the outer surfaces (the first plate surface 21 and the second plate surface 23) perpendicular to the stacking direction LD in the sensor element, the one outer surface (the first plate surface 21 in the embodiments) being on the side where the opening of the introduction flow path IP is provided, to the reference gas flow path CP is represented as a distance $D_A$, and a distance from the other outer surface (the second plate surface 23 in the embodiments) to the reference gas flow path CP is represented as a distance $D_B$, $D_A < D_B$ is desirably satisfied (see FIG. 4). When the length of the introduction flow path IP is further shortened as described above, the effect of stabilizing the performance of the gas sensor by stabilizing the flow of the reference gas to the reference electrode 442 can be enhanced.

It is noted that the distance $D_A$ from one outer surface, in which openings of the introduction flow path IP are provided, of the outer surfaces perpendicular to the stacking direction LD of the sensor element to the reference gas flow path CP refers to a distance as follows. That is, the distance $D_A$ refers to a distance from the one outer surface to an inner wall surface at the one outer surface side, of inner wall surfaces of the reference gas flow path CP perpendicular to the stacking direction LD (in the embodiments, the surface, of the solid electrolyte layer 430, on which the reference electrode 442 is formed). In addition, the distance $D_B$ from the other outer surface, of the outer surfaces perpendicular to the stacking direction LD of the sensor element, to the reference gas flow path CP refers to a distance as follows. That is, the distance $D_B$ refers to a distance from the other outer surface to an inner wall surface at the other outer surface side, of inner wall surfaces of the reference gas flow path CP perpendicular to the stacking direction LD (in the embodiments, the surface, of the insulating layer 423, with which the gas flow path formation layer 422 contacts).

From the standpoint that the length of the introduction flow path introducing the reference gas into the reference gas flow path CP is further shortened, it is desirable that $D_A < D_C$ is satisfied in the sensor element. Here, as described above, the distance $D_A$ is a distance from one outer surface, in which the opening of the introduction flow path IP is provided, of outer surfaces perpendicular to the stacking direction LD of the sensor element, to the reference gas flow path CP. In addition, a distance $D_C$ is a distance from an end portion, on a side closer to the introduction flow path IP, of end portions of the sensor element in the longitudinal direction, to the reference gas flow path CP (see FIG. 4).

However, it is not essential that $D_A < D_B$ is satisfied and $D_A < D_C$ is satisfied. Even if these relationships are not satisfied, it is possible to obtain the aforementioned effect by forming, as a flow path for guiding the reference gas to the reference gas flow path CP, the introduction flow path IP extending in the stacking direction from the opening provided in the first plate surface 21 that is the surface of the sensor element 4 to the reference gas flow path CP.

Modified Embodiment 2

Although in the above embodiments, the reference gas flow path CP is formed by the introduction hole 70 that is a through-hole provided in the gas flow path formation layer 422, the reference gas flow path CP may have a different structure. For example, the introduction hole 70 provided in the gas flow path formation layer 422 may not be a through-hole but a recess that does not penetrate through the insulating layer 423 side.

Figure 6:
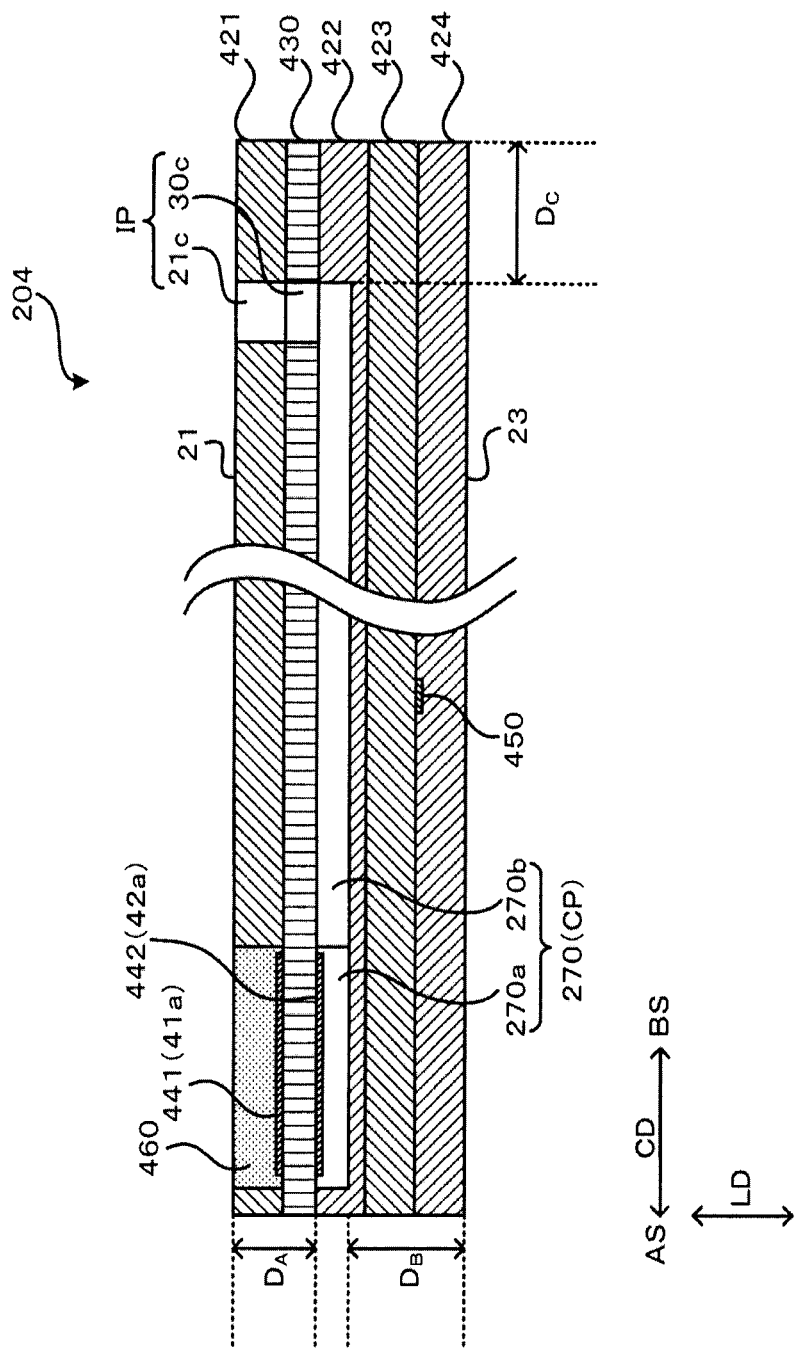
FIG. 6 is a sectional view of the sensor element.

FIG. 6 is a sectional view, as in FIG. 4, showing the structure of a sensor element 204 as an example of a modified embodiment in which a recess shape is applied to the introduction hole 70. The sensor element 204 is used in the gas sensor 2, like the sensor element 4 of the first embodiment, and the structure of the sensor element 204 is similar to that of the sensor element 4 except the structure regarding the gas flow path formation layer 422. Hereinafter, the same reference numbers are assigned to the same parts as those of sensor element 4, and a detailed description thereof is omitted.

In the sensor element 204, the gas flow path formation layer 422 has a recess 270 instead of the introduction hole 70 that is a through-hole. The recess 270 is the same as the introduction hole 70 in shape as seen from the first plate surface 21 side, and includes a reference chamber recess 270a that is formed in a rectangular shape in a plan view, and a ventilation groove 270b extending from the reference chamber recess 270a to the rear side BS. The recess 270 forms the reference gas flow path CP in the sensor element 204, and the reference gas is introduced into the recess 270 through the introduction flow path IP formed by the through-holes 21c, 30c. This structure also provides the same effect as in the first embodiment. It is noted that when the reference gas flow path CP is formed by the recess provided in the gas flow path formation layer 422, the insulating layer 423 can be omitted.

Modified Embodiment 3

Although in the above-described embodiments, the entirety of the solid electrolyte layer 430 is formed from a solid electrolyte, the solid electrolyte layer 430 may be formed in a different manner. The solid electrolyte layer may at least partially include a solid electrolyte portion that is formed from a solid electrolyte and that is held by the detection electrode 441 (the first electrode portion 41a) and the reference electrode 442 (the second electrode portion 42a).

Figure 7:
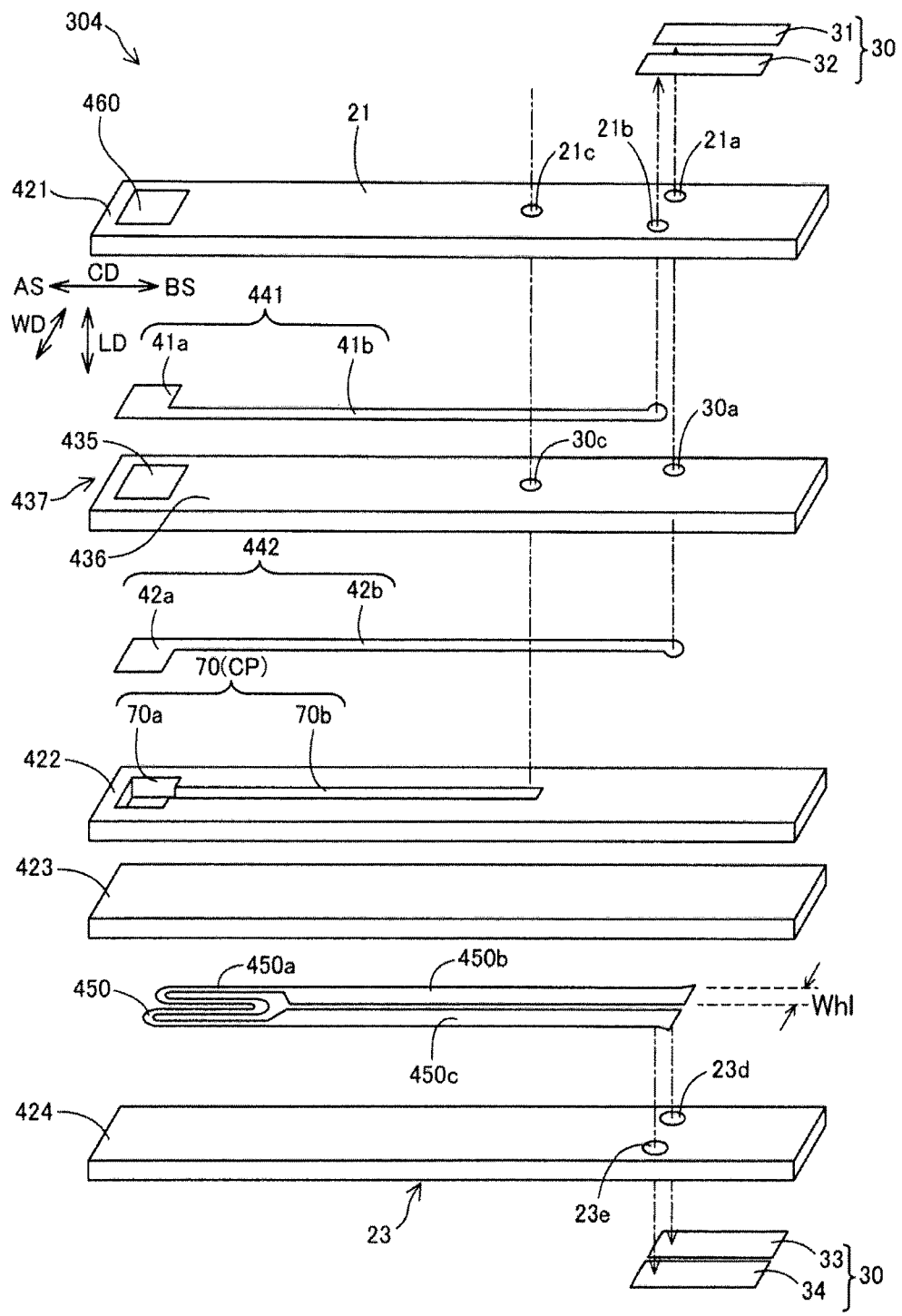
FIG. 7 is an exploded perspective view of the sensor element.
Figure 8:
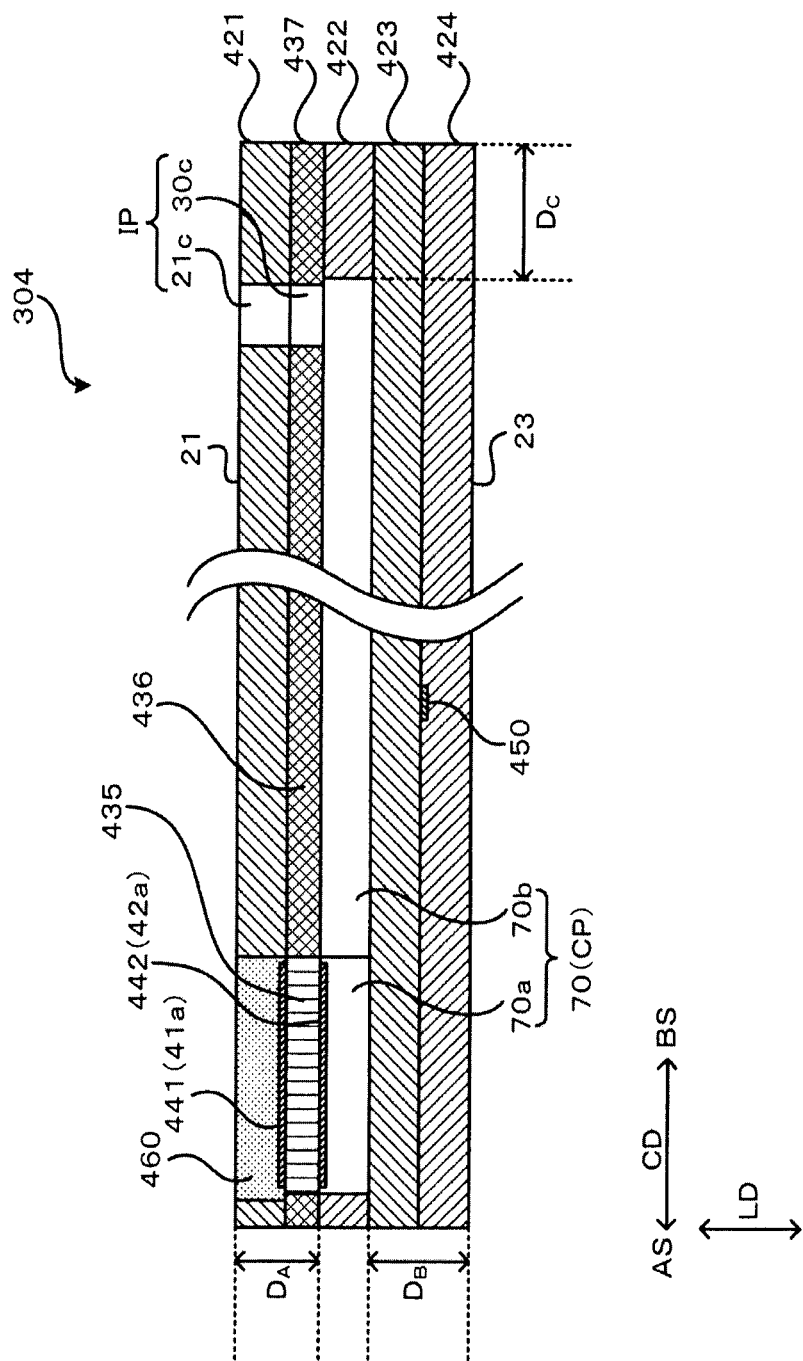
FIG. 8 is a sectional view of the sensor element.

FIG. 7 is an exploded perspective view of a sensor element 304 according to a modified embodiment of the present invention, as in FIG. 2. FIG. 8 is a sectional view showing the structure of the sensor element 304 of the modified embodiment, as in FIG. 4. The sensor element 304 of the present modified embodiment is used in the gas sensor 2, like the sensor element 4 of the first embodiment, and has the same structure as the sensor element 4 except that a solid electrolyte layer 437 is included instead of the solid electrolyte layer 430. Hereinafter, the same reference numbers are assigned to the same parts as those of sensor element 4, and a detailed description thereof is omitted.

In the sensor element 304, the solid electrolyte layer 437 includes a solid electrolyte portion 435 and an insulating substrate 436. The solid electrolyte portion 435 is formed from a solid electrolyte similar to the solid electrolyte forming the solid electrolyte layer 430 of the first embodiment. The insulating substrate 436 is a dense layer that electrically insulates between adjacent layers. The insulating substrate 436, like the insulating layers 421, 423, 424, is formed from an insulating ceramic, for example, an insulating ceramic including alumina as a principal component.

The front side AS of the insulating substrate 436 has a rectangular hole that penetrates through the insulating substrate 436 in the thickness direction (the stacking direction LD) thereof, and the solid electrolyte portion 435 is formed in the hole. As shown in FIG. 8, the solid electrolyte portion 435, when being projected in the stacking direction LD, is provided by penetrating through the insulating substrate 436 in a region that overlaps with the first electrode portion 41a of the detection electrode 441, the second electrode portion 42a of the reference electrode 442, the reference chamber hole 70a, and the porous protection layer 460. In addition, the insulating substrate 436, like the solid electrolyte layer 430, has the through-holes 30a, 30c that penetrate through the insulating substrate 436 in the thickness direction (the stacking direction LD) thereof.

The above structure also provides the same effect as that in the first embodiment. Further, as compared with the structure of the first embodiment in which the entirety of the solid electrolyte layer 430 is formed from a solid electrolyte, the strength of the entire sensor element 304 can be enhanced, and as a result, the strength of the entire gas sensor can be enhanced. This is because the insulating ceramic forming the insulating substrate 436 is generally higher in strength than the solid electrolyte forming the solid electrolyte portion 435. In addition, as compared with the structure of the first embodiment in which the entirety of the solid electrolyte layer 430 is formed from a solid electrolyte, the temperature of the solid electrolyte portion can be quickly increased to a predetermined active temperature when the gas sensor is used. This is because the insulating ceramic forming the insulating substrate 436 generally has a higher coefficient of thermal conductivity than the solid electrolyte forming the solid electrolyte portion 435.

Modified Embodiment 4

Although in the above embodiments, the cross-sectional shape perpendicular to the stacking direction LD in the introduction flow path IP is a circular shape, the cross-sectional shape may be a shape other than the circular shape. However, from the standpoint that concentration of stress is caused in the sheet-like member by providing through-holes (through-holes 21c, 30c, and the like) for forming the introduction flow path IP in a sheet-like member forming the sensor element, and as a result, a reduction in bending strength of the sensor element is suppressed, the cross-sectional shape is desirably an elliptical shape or a circular shape. A circular shape is more desirable.

Modified Embodiment 5

Although in the above embodiments, the gas sensor is an oxygen concentration sensor, the gas sensor may be a sensor other than the oxygen concentration sensor. A sensor that detects different types of gases, such as NOx, in an exhaust gas may be adopted. As long as a sensor includes a concentration cell having the pair of electrodes stacked on both sides of a solid electrolyte having ion conductivity and generating an electromotive force due to a concentration difference (partial pressure difference) of a specific gas component on each electrode, this structure also provides the same effect as described above by applying the present invention to the sensor.

The present invention is not limited to the above embodiments, examples, and modifications/variations and can be embodied in various forms without departing from the scope of the present invention. For example, it is feasible to appropriately replace or combine any of the technical features of the aspects of the present invention described in "Summary of the Invention" and the technical features of the embodiments, examples and modifications/variations of the present invention in order to solve part or all of the above-mentioned problems or achieve part or all of the above-mentioned effects. Any of these technical features, if not explained as essential in the present specification, may be deleted as appropriate.

DESCRIPTION OF REFERENCE NUMERALS 2 gas sensor
4, 104, 204, 304 sensor element
6 ceramic sleeve
8 detection portion
10 metal terminal member
21 first plate surface
21a to 21c through-hole
23 second plate surface
23d, 23e through-hole
30 electrode terminal portion
30a, 30c through-hole
31 to 34 electrode terminal portion
38 metal shell
39 screw portion
40 rear end portion
41a first electrode portion
41b first lead portion
42a second electrode portion
42b second lead portion
43 internal protector
44 sheath
45 external protector
46 lead wire
50 grommet
52 shelf portion
53 ceramic holder
54 through-hole
56 powder-charged layer
57 crimping packing
58 through-hole
59 filter unit
61 lead wire insertion hole
62 rear side end surface
63 rear side separator
65a insertion portion
65b groove portion
66 front side separator
67 flange portion
68 front side end surface
69 holding member
70 introduction hole
70a reference chamber hole
70b ventilation hole
270 recess
270a reference chamber recess
270b ventilation groove
421, 423, 424 insulating layer
422 gas flow path formation layer
430, 437 solid electrolyte layer
435 solid electrolyte portion
436 insulating substrate
441 detection electrode
442 reference electrode
450 heater
450a heating portion
450b, 450c heater lead portion
460 porous protection layer

The invention claimed is:

1. A gas sensor element comprising:
a solid electrolyte layer;
a detection electrode provided on one surface of the solid electrolyte layer and exposed to a gas to be measured;
a reference electrode provided on another surface of the solid electrolyte layer and exposed to a reference gas;
a first layer provided on a side where the other surface of the solid electrolyte layer is present, and having a reference gas flow path that introduces the reference gas into the reference electrode; and
a heater layer provided on a side opposite to a side where the solid electrolyte layer is provided with respect to the first layer, the heater layer including a heating portion for heating the solid electrolyte layer, wherein
the solid electrolyte layer, the first layer and the heater layer are stacked,
an introduction flow path is formed in the gas sensor element as a flow path for guiding the reference gas from an outer surface of the gas sensor element to the reference gas flow path,
the introduction flow path has an opening provided at the outer surface that is perpendicular to a stacking direction of the gas sensor element and is provided on a side opposite to the side where the heater layer is provided with respect to the first layer, and
the introduction flow path extends in the stacking direction from the opening to the reference gas flow path.

2. The gas sensor element according to claim 1, wherein
a plurality of the openings are provided, and
the introduction flow path is composed of a plurality of divided flow paths extending in the stacking direction from the respective openings to the reference gas flow path.

3. The gas sensor element according to claim 2, wherein the plurality of openings are provided at different positions with respect to a longitudinal direction of the gas sensor element.

4. The gas sensor element according to claim 1, wherein $D_A < D_B$ is satisfied, where $D_A$ is a distance from the outer surface, in which the opening is provided, to the reference gas flow path and $D_B$ is a distance from another outer surface of the gas sensor element to the reference gas flow path.

5. The gas sensor element according to claim 1, wherein $D_A < D_C$ is satisfied, where $D_A$ is a distance from the outer surface, in which the opening is provided, to the reference gas flow path and $D_C$ is a distance from an end portion of the gas sensor element on a side closer to the introduction flow path in a longitudinal direction to the reference gas flow path.

6. The gas sensor element according to claim 1, wherein, the solid electrolyte layer includes: an insulating substrate formed from an insulating ceramic; and a solid electrolyte portion formed from a solid electrolyte and the solid electrolyte portion is placed in a hole formed in the insulating substrate in a region that overlaps with the detection electrode and the reference electrode in the stacking direction.

7. A gas sensor comprising the gas sensor element according to claim 1.

* * * * *